(12) United States Patent
Gutman et al.

(10) Patent No.: US 6,696,568 B2
(45) Date of Patent: Feb. 24, 2004

(54) PROCESS AND INTERMEDIATES FOR PRODUCTION OF CABERGOLINE AND RELATED COMPOUNDS

(75) Inventors: Arie L. Gutman, Haifa (IL); Gennadiy Nisnevich, Haifa (IL); Igor Ruchman, Kyriat Yam (IL); Boris Tishin, Haifa (IL); Alex Vilensky, Haifa (IL); Boris Pertsikov, Nesher (IL)

(73) Assignee: Finetech Ltd., Haifa (IL)

( * ) Notice: Subject to any disclaimer, the term of this patent is extended or adjusted under 35 U.S.C. 154(b) by 0 days.

(21) Appl. No.: 09/834,657

(22) Filed: Apr. 16, 2001

(65) Prior Publication Data

US 2002/0177709 A1 Nov. 28, 2002

(51) Int. Cl.$^7$ ............................................. C07D 457/04
(52) U.S. Cl. .......................................... 546/14; 546/69
(58) Field of Search ...................... 546/14, 69

(56) References Cited

U.S. PATENT DOCUMENTS

| 4,526,892 A | 7/1985 | Salvati et al. ................ 514/288 |
| 5,382,669 A | 1/1995 | Candiani et al. .............. 546/69 |

FOREIGN PATENT DOCUMENTS

| GB | 2103603 | 2/1983 |

OTHER PUBLICATIONS

Enzo Brambilla et al.; Eur. J. Med. Chem. 24 (1989) pp. 421–426.
Ilaria Candiani et al.; Syn. Lett., 1995, pp. 605–606.

*Primary Examiner*—John M. Ford
*Assistant Examiner*—Hong Liu
(74) *Attorney, Agent, or Firm*—Birch, Stewart, Kolasch & Birch, LLP

(57) ABSTRACT

A process for preparation of N-(ergoline-8β-carbonyl)ureas of the formula [I] their stereoisomers as well as acid addition salts thereof which process comprises silylating an ergoline-8β-carboxamide of the formula [2],

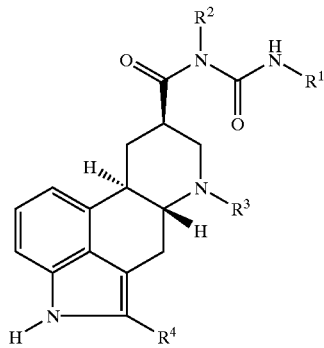

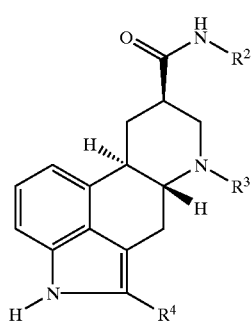

their stereoisomers as well as metal or ammonium salts or acid addition salts thereof and reacting the resultant product with an isocyanates $R^1N=C=O$ [5]

wherein $R^1$ is selected from alkyl having from 1 to 4 carbon atoms, cyclohexyl, phenyl, and dimethylamino alkyl group —$(CH_2)_nNMe_2$ in which n is an integer, $R^2$ is selected from hydrogen, alkyl having from 1 to 4 carbon atoms, cyclohexyl, phenyl, dimethylamino alkyl group —$(CH_2)_nNMe_2$ in which n is an integer, pyridyl, pyrimidyl, pyrazinyl, pyridazinyl, thiazolyl or thiadiazolyl, $R^3$ represent a hydrocarbon group having from 1 to 4 carbon atoms, and $R^4$ is selected from hydrogen, halogen, methylthio and phenylthio group;; followed by desilylation.

This novel approach provides an efficient method for preparation of N-(ergoline- 8β-carbonyl)ureas of the formula [I] which can be useful as anty-Parkisons drugs and prolactin inhibitors. One of the most potent antiprolactinic agent of the class of compounds prepared according to the present invention is Cabergoline.

Silylated ergolines, which are obtained as intermediates in the process of the present invention, are novel compounds and represent a further aspect of the invention.

20 Claims, No Drawings

PROCESS AND INTERMEDIATES FOR PRODUCTION OF CABERGOLINE AND RELATED COMPOUNDS

FIELD OF THE INVENTION

This invention relates to a new process for the preparation of dopamine agonists such as Cabergoline, to some novel intermediates used in this process and to their preparation.

BACKGROUND OF THE INVENTION

N-(Ergoline-8β-carbonyl) ureas of formula [1]

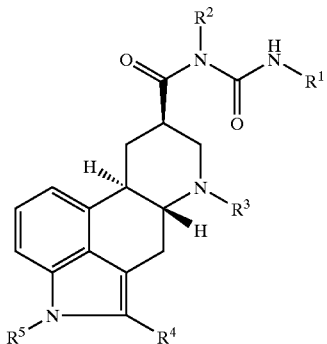

[1]

wherein $R^1$ represents an alkyl group having from 1 to 4 carbon atoms, a cyclohexyl group or a phenyl group or a dimethylamino alkyl group —$(CH_2)_nNMe_2$ in which n is an integer, $R^2$ represents any of the groups which $R^1$ may represent, or a hydrogen atom or a pyridyl, pyrimidyl, pyrazinyl, pyridazinyl, thiazolyl or thiadiazolyl residue, $R^3$ represents a hydrocarbon group having from 1 to 4 carbon atoms, $R^4$ represents a hydrogen or a halogen atom or a methylthio or phenylthio group and $R^5$ represents a hydrogen atom or a methyl group; have shown potent dopamine agonist properties and have been useful as anti-Parkinson drugs and as prolactin inhibitors (U.S. Pat. No. 5,382,669 and Eur. J. Med. Chem., 1989, v. 24, 421).

One of the most potent prolactin inhibitor of this class is 1-(6-alkylergoline-8β-carbonyl)-1-[3-(dimethylamino) propyl]-3-ethylurea (international non-proprietary name Cabergoline) [1a] (Eur. J. Med. Chem., 1989, v.24, 421) which was firstly prepared by reaction of 6-alkylergoline-8β-carboxylic acid [7] with 1-[3-(dimethylamino)propyl]-3-ethylcarbodiimide (U.S. Pat. No. 4,526,892) (Scheme 1).

Scheme 1

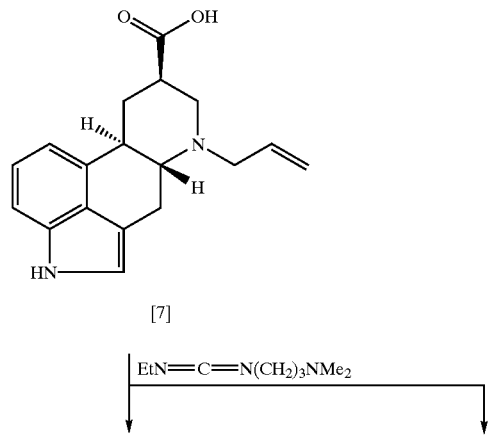

[7]

| EtN═C═N(CH₂)₃NMe₂

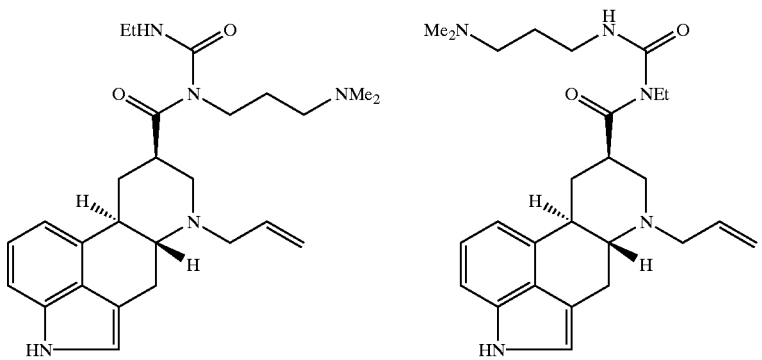

Cabergoline [1a]          By-product [8]

In this case both regioisomers [1a] and [8] were obtained and the yield of the isolated Cabergoline [1a] is low as a consequence of isolation difficulties.

Another method for Cabergoline preparation (Eur. J. Med. Chem., 1989, v, 24, 421 and BP 2,13,603) was based on the direct reaction of N-[3-(dimethylamino)propyl]-6-alkylergoline-8β-carboxamide [2a] with ethyl isocyanate (Scheme 2):

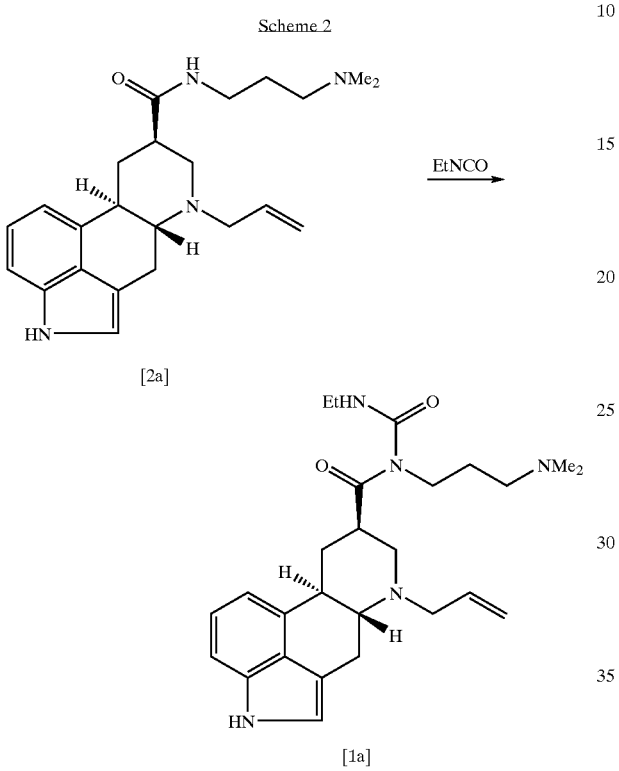

However, this approach required large amounts of ethyl isocyanate (up to 40 eq.) and reflux in toluene for several days. The use of large quantities of toxic isocyanate under drastic reaction conditions represented the major limitation for the large-scale preparation of Cabergoline by this route.

The method proposed in U.S. Pat. No. 5,382,669 and Syn. Lett., 1995, 605 is based is on copper salts catalyzed reaction of ethyl isocyanate with carboxamide [2a] using phosphorous ligands. Drawbacks of this approach are the use of heavy metal ions or, the final step of the synthesis and decreasing chemoselectivity with increasing conversion of this reaction.

SUMMARY OF THE INVENTION

All the previously disclosed methods for the preparation of Cabergoline present serious drawbacks for producing material suitable for use as a pharmaceutical drug. A desirable goal, met by the present invention, has been to devise a new synthetic method, which avoids use of heavy metal salts, and which cleanly produces the desired Cabergoline [1a] under mild reaction conditions, avoiding tedious and expensive purification steps.

The present invention provides a commercially acceptable process for producing N-(ergoline-8β-carbonyl)ureas of formula [I]:

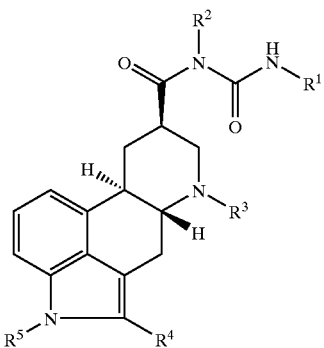

including their stereoisomers as well as acid addition salts thereof, wherein $R^1$ is selected from alkyl having from 1 to 4 carbon atoms, cyclohexyl, phenyl, and (dimethylamino alkyl group —$(CH_2)_n NMe_2$ in which n is an integer, $R^2$ is selected from hydrogen, alkyl having from 1 to 4 carbon atoms, cyclohexyl, phenyl, dimethylamino alkyl group —$(CH_2)_n NMe_2$ in which a is an integer, pyridyl, pyrimidyl, pyrazinyl, pyridazinyl, thiazolyl or thiadiazolyl , $R_3$ represents a hydrocarbon group having from 1 to 4 carbon atoms, and $R^4$ is selected from hydrogen halogen, methylthio and phenylthio group;

which process comprises silylating an ergoline-8-carboxamide of formula [2],

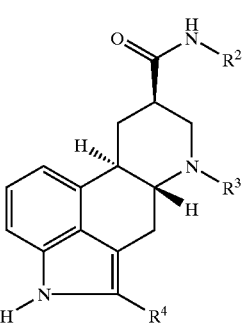

including stereoisomers as well as metal or ammonium salts or acid addition salts thereof, wherein $R^1$, $R^2$, $R^3$ and $R^4$ are as defined above, reacting the obtained product with isocyanate of the formula [5]:

$$R^1-N=C=O \qquad [5]$$

Followed by Desilylation

This novel approach was used for the preparation of the known antiprolactinic and anti-Parkinson agent Cabergoline [1a] and related compounds.

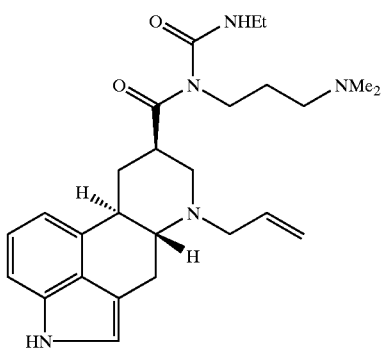

[1a]

Other features and advantages will be apparent from the specification and claims.

DETAILED DESCRIPTION OF THE INVENTION

The present invention describes a novel process for the preparation of N-(ergoline-8β-carbonyl)urea compounds of formula [I]. Particularly, the present invention utilizes the silylation of of ergoline-8β-carboxamide [2] in order to selectively activate it's amide group in the subsequent reaction with isocyanate.

This novel approach has the following advantages:

Silylated ergoline-8β-carboxamides react with isocyanates to give, after desilylation of intermediates, the desired N-(ergoline-8β-carbonyl)ureas [I] with high yield and purity.

Reagents used for silylation and desilylation are not toxic, commercially available and inexpensive.

Although any silylating agents, suitable for silylating amides, can be used for silylating ergoline-8β-carboxamide [2], a compound of formula [3] is preferably used for this purpose to give intermediate N-silylamide of the formula [4], tautomers or mixtures thereof, stereoisomers, as well as addition salts thereof; intermediate [4] reacts with isocyanate of formula [5]:

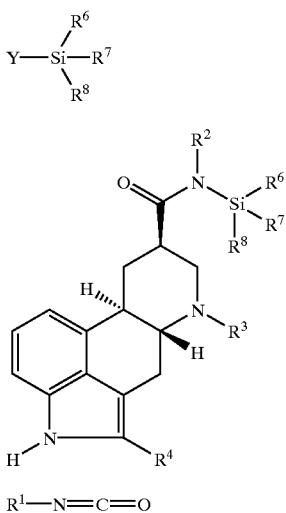

[3]

[4]

[5]

wherein $R^6$, $R^7$ and $R^8$ may be the same or different and are selected from the group consisting of alkyl having from 1 to 6 carbon atoms, aryl and aralkyl radicals;

Y is selected from the group consisting of chloro, bromo, iodo, (haloalkyl)-sulfonyloxy, alkylsulfonyloxy, arylsulfonyloxy, (trialkylsilyloxy)sulfonyloxy, imidazolyl, N-acyl-N-alkylamino, N-acyl-N-(trialkylsily) amino, (trialkylsilyl)-amino, N,N-dialkylamino, isopropenyloxy, 1-alkoxy-1-alkenyloxy and trichloroacetoxy radicals;

and $R^1$, $R^2$, $R^3$ and $R^4$ are as defined above, to give O-silylated N-[ergoline-8β-carbonyl]urea represented by formula [6]:

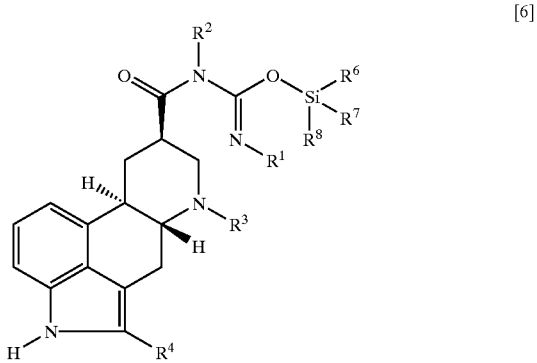

[6]

including, tautomers or mixtures thereof, stereoisomers, as well as addition salts thereof, wherein $R^1$, $R^2$, $R^3$, $R^4$, $R^6$, $R^7$ and $R^8$ are as defined above; following desilylation of the above compound(s) to obtain the desired N-(ergoline-8β-carbonyl)urea [I], which can be converted into acid addition salts thereof.

The silylating agent may be used in a 0.5 to 10 fold molar amount, preferably from 0.9 to 5 fold molar amount, relative to the amount of the ergoline-8β-carboxamide [2]. Preferably, silylating agents are selected from trimethylsilyl trifluoromethanesulfonate, trimethylsilyl methanesulfonate, trimethylsilyl benzenesulfonate, trimethylsilyl chlorosulfonate, trimethylsilyl chloride, bromide or iodide, trimethylsilyl trichloroacetate and trifluoroacetate, 1-(trimethylsilyl)imidazol, 1-(trimethylsilyl)-1,2,4-triazole, 1-(trimethylsilyl)-1H-benzotriazole, 1-(trimethylsilyl)-2-pyrrolidinone, N-methyl-N-(trimethylsilyl) trifluoroacetamide, methyl trimethylsilyl dimethylketene acetal, bis(trimethylsilyl)sulfate, N,O-bis(trimethylsilyl) acetamide and bis(trimethylsilyl)trifluoroacetamide.

The silylation reaction may be cared out from –50° C. to the reflux temperature of the reaction mixture. Preferably, the silylation is carried out from 0° to 50° C.

Organic or inorganic acids or salts may accelerate the silylation. Examples of such acids include mineral acids such as sulfuric acid or hydrogen halide. Examples of salts include metal halides, tertiary ammonium halides, ammonium halides, ammonium sulfate, pyridine or it's derivatives hydrohalides. However, preferably, organic or inorganic bases accelerate the silylation reaction. Examples of organic bases are tertiary amines, sterically hindered secondary amines, pyridine or there derivatives, 1,5-diazabicyclo[4.3.0]non-5-ene (DBN), 1,8-diazabicyclo[5.4.0]undec-7-ene (DBU) or mixture thereof. Examples of tertiary amines include 1-ethylpiperidine, 1-butylpyrrolidine, diisopropylethylamine, triethylamine, N,N,N',N'-tetramethylethylenediamine, 1,4-diazabicyclo[2.2.2]octane or mixture thereof. Examples of sterically hindered secondary amines are diisopropylamine, dicyclohexylamine, 2,2,6,6-tetramethylpiperidine or mixture thereof. Examples of pyridine derivatives are 4-dimethylaminopyridine (DMAP), 4-(4-methylpiperidino)pyridine and 4-pyrrolidinopyridine or mixture thereof.

The solvent for the silylation reaction may be any suitable aprotic organic solvent provided it does not inhibit the reaction. Examples thereof include aromatic hydrocarbons such as benzene, toluene and xylene, chlorobenzene, o-dichlorobenzene, m-dichlorobenzene and bromobenzene; hydrocarbon halides such as dichloromethane and chloroform; ether solvents such as ether, isopropyl ether, tert-butyl methyl ether, 1,2-dimethoxyethane, 1,2-diethoxyethane, tetrahydrofuran (THF); ester-type solvents such as ethyl acetate, isopropyl acetate, butyl acetate; or highly polar aprotic organic solvents such as acetonitrile, N,N-dimethylformamide (DMF), N,N-dimethylacetamide or 1-methylpyrrolidinone (NMP).

The resultant silylated product may be used in the following step after isolation from the reaction mass, or may be subjected to the subsequent step without isolation.

After silylation, the resultant product is reacted with a compound of formula [5], which may be used in a 1 to 10 fold molar amount, preferably 2 to 5 fold molar aunt relative to the amount of the ergoline-8β-carboxamide [2]. The reaction may be carried out at temperature from −50° C. to reflux temperature of the reaction mixture. Preferably, the reaction is carried out at 0–50° C. without a isolating silylated ergoline-8β-carboxamide from the reaction mass.

The reaction of silylated ergoline-8β-carboxamide with isocyanate may be carried out without solvent but preferably, the reaction is carried out in any organic aprotic solvent which does not inhibit the reaction. Examples thereof include aromatic hydrocarbons such as benzene, toluene and xylene, chlorobenzene, o-dichlorobenzene, m-dichlorobenzene and bromobenzene; hydrocarbon halides such as dichloromethane and chloroform; ether solvents such as ether isopropyl ether, tert-butyl methyl ether, 1,2-dimethoxyethane, 1,2-diethoxyethane, tetrahydrofuran (THF); ester-type solvents such as ethyl acetate, isopropyl acetate, butyl acetate; or highly polar aprotic organic solvents such as acetonitrile, N,N-dimethylformamide (DMF),N,N-dimethylacetamide or 1-methylpyrrolidinone (NMP).

Optionally, the reaction of silylated ergoline8β-carboxamide with isocyanate may be accelerated by transition metal(s) salt(s) and/or coordination compound(s) or fluoride-ions. Examples of the said transition metals include copper or zinc. Preferably, the said transition metal(s) salt(s) are copper and/or zinc halides. Preferably the said ligands in the coordination compound(s) with transition metal(s) contain phosphorous, nitrogen and/or oxygen atoms. Examples of the ligands include triarylphosphines, pyridine or it's derivatives, tertiary amines, nitriles, amides and ether-type compounds.

The desilylation can be carried out by, for example, using fluoride salts optionally in the presence of phase transfer catalysts. Examples of the said fluoride salt include tetraalkylammonium fluoride, benzyltrialkylammonium fluoride and alkali metal fluoride. Examples of the said phase transfer catalysts include tetraalkylammonium salts, benzyltrialkylammonium salts and crown ethers.

Cabergoline [1a] may be prepared from amide [2a] according to Scheme 3:

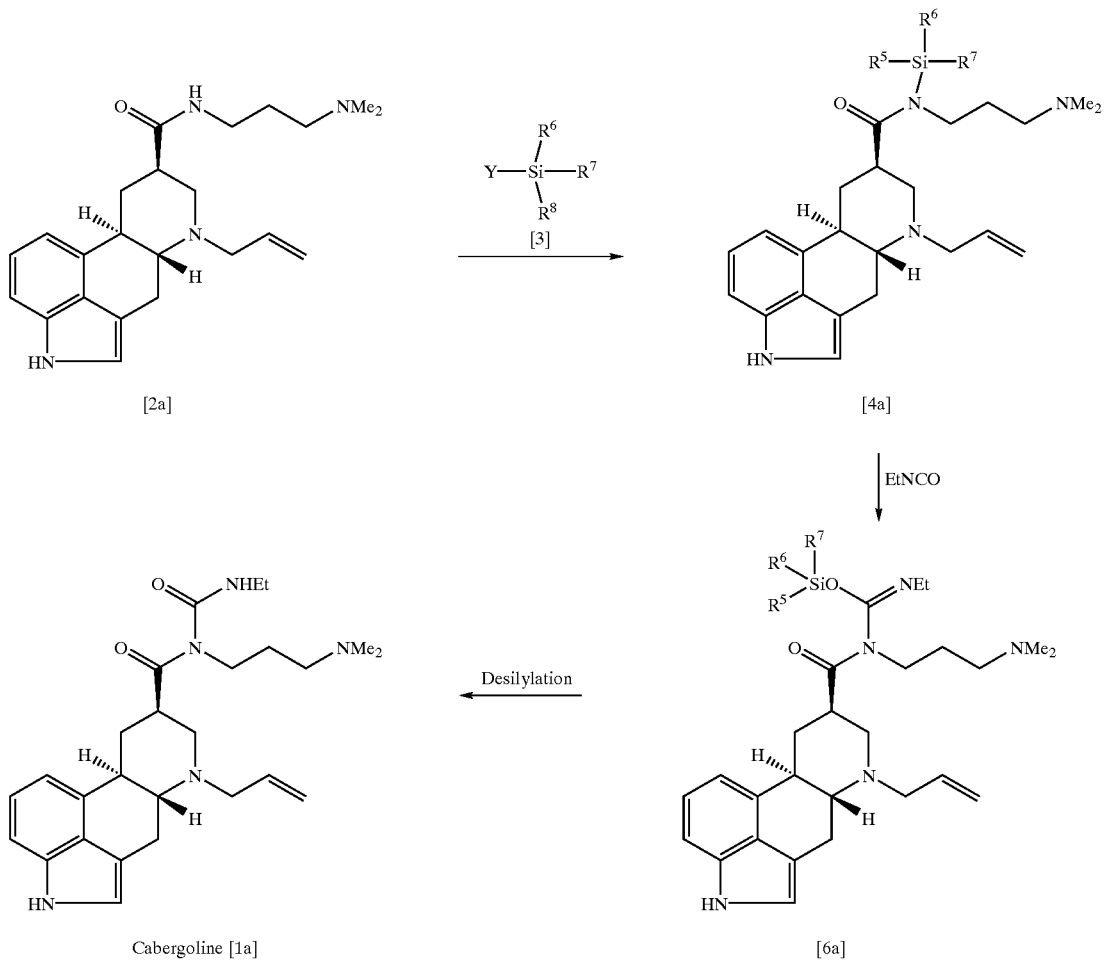

Scheme 3

Cabergoline [1a]

[6a]

The invention will be further described in more detail with the following non-limiting examples,

EXAMPLE 1

Scheme 4

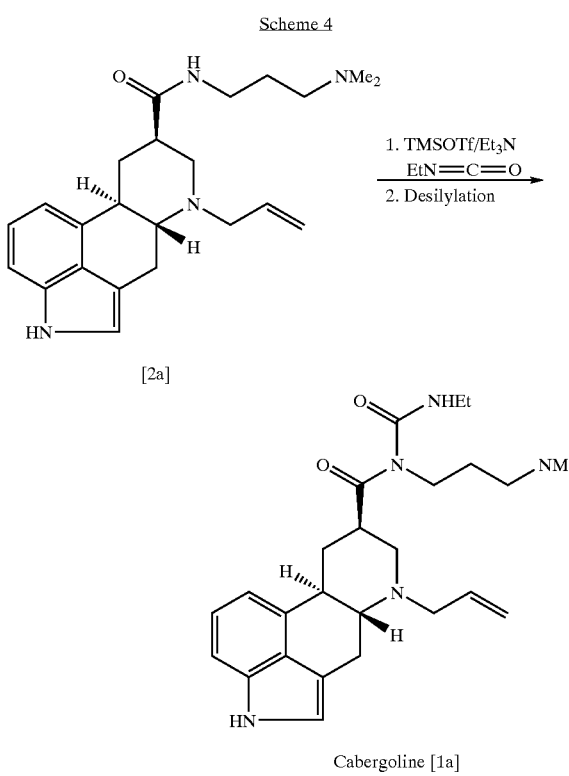

[2a]

Cabergoline [1a]

Typical Procedure A

A tree-necked round-bottom flask fitted with a reflux condenser (optional), thermometer and septum was evacuated, dried and flushed with dry nitrogen or argon. Solution of amide [2a] (3.00 g, 7.9 mmol) and triethylamine (1.11 g, 11.0 mmol) in dichloromethane (30 mL) was cooled to 0÷C. and trimethylsilyl trifluoromethanesulfonate (1.84 g, 8.3 mmol) was added dropwise during 5 min . The resulted mixture was stirred for 5 hours at 0÷C. Then ethyl isocyanate (2.25 g, 31.6 mmol) was added to the mixture. The resulted mixture was stirred for 24 hours at 15÷C. and evaporated under reduced pressure. The residue was dissolved in THF (30 ml) and triethylamine trihydrofluoride (1.40 g, 8.7 mmol) A as added to the solution. The solution was stirred for 2–3 hours (TLC monitoring) at room temperature. Diethyl ether (60 mL) and sat aq sodium bicarbonate solution (50 mL, careful addition) were added and the resulted two-phase mixture was stirred for 20 min. Then the phases were separated and the aq phase was washed with diethyl ether. The combined organics were washed with water and brine, dried over sodium sulfate, filtered and evaporated under reduced pressure. The residue was purified on a short silica gel column followed by crystallization from diethyl ether and vacuum desiccation to give 3.24 g (90%) of [1a] as a white solid.

Typical Procedure B

The solution of amide [2a], triethylamine and ethyl isocyanate in dichloromethane was cooled to 0÷C. under argon and trimethylsilyl trifluoromethanesulfonate (1.84 g, 8.3 mmol) in dichloromethane (5 mL) was added dropwise. The resulted mixture was stirred for 20 min at 0÷C. and for additional 24 h at 15÷C. Work-up and purification of the final product were carried out as described in the procedure A.

EXAMPLE 2–15

Scheme 5

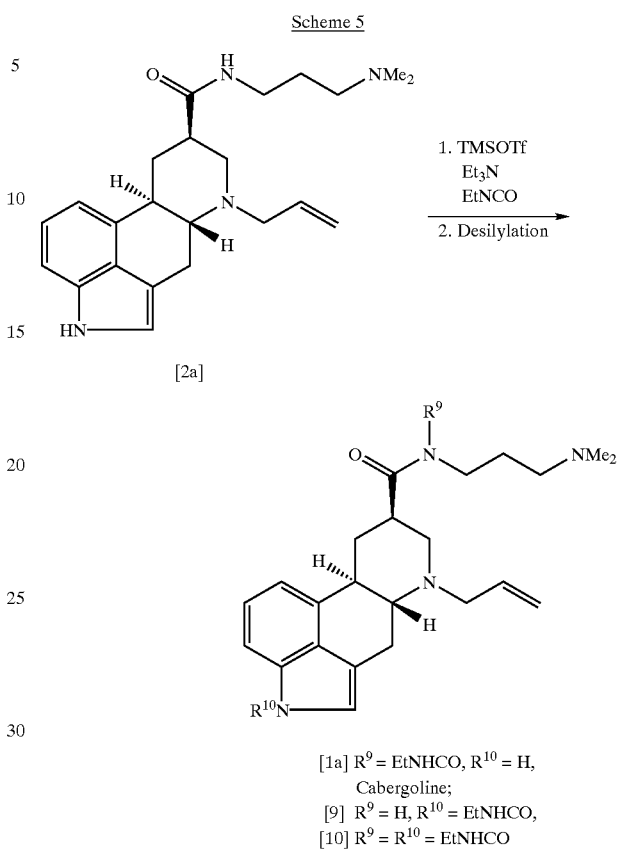

[1a] $R^9$ = EtNHCO, $R^{10}$ = H, Cabergoline;
[9] $R^9$ = H, $R^{10}$ = EtNHCO,
[10] $R^9$ = $R^{10}$ = EtNHCO

TABLE 1

Reaction between [2a] and ethyl isocyanate. Effect of solvent, temperature and amounts of trimethylsilyl trifluoromethanesulfonate (TMSOTf) and ethyl isocyanate on reaction yield and selectivity

| Ex. no. | TMSOTf (eq.) | EtNCO (eq.) | Solvent (procedure)[a] | T, °C. (time, h) | Yield of 1a, % | 1a/9/10[d] |
|---|---|---|---|---|---|---|
| 2 | 1.05 | 1 | CH$_2$Cl$_2$ (A) | 0(5), rt(24) | 62[b] | 99.4:0.3:0.3 |
| 3 | 1.05 | 2 | CH$_2$Cl$_2$ (A) | 0(5), rt(24) | 70[b] | 99.0:0.3:0.7 |
| 4 | 1.05 | 3–5 | CH$_2$Cl$_2$ (A) | 0(5), 15(24) | 90–95[b] | 99.7:0:0.3 |
| 5 | 1.05 | 3–5 | CH$_2$Cl$_2$ (B) | 15(24) | 88–92[b] | 99.6:0:0.4 |
| 6 | 1.1 | 3–5 | CH$_2$Cl$_2$ (A) | 0(5), rt(24) | 86[b] | 99.1:0.1:0.7 |
| 7 | 1.1 | 3–5 | CH$_2$Cl$_2$ (A) | 0(5), 40(24) | 83[b] | 94.0:0.5:5.2 |
| 8 | 1.2 | 3–5 | CH$_2$Cl$_2$ (A) | 0(5), rt(24) | 78[b] | 98.2:0.8:1.0 |
| 9 | 1.5 | 3–5 | CH$_2$Cl$_2$ (A) | 0(5), rt(24) | 69[b] | 96.5:0.5:3.0 |
| 10 | 2.0 | 3–5 | CH$_2$Cl$_2$ (A) | 0(5), rt(24) | 64[c] | 85.0:1.0:13.7 |
| 11 | 2.5 | 3–5 | CH$_2$Cl$_2$ (A) | 0(5), rt(24) | 56[c] | 72.9:1.1:25.3 |
| 12 | 1.1 | 3 | Et$_2$O (A) | 0(5), rt(24) | 65[c] | 99.3:0.3:0.4 |
| 13 | 1.1 | 3 | Et$_2$O (B) | rt(24) | 65[c] | 99.1:0.3:0.6 |
| 14 | 1.5 | 3 | Et$_2$O (A) | 0(5), rt(24) | 58[c] | 95.5:1.0:3.5 |

TABLE 1-continued

Reaction between [2a] and ethyl isocyanate. Effect of solvent, temperature and amounts of trimethylsilyl trifluoromethanesulfonate (TMSOTf) and ethyl isocyanate on reaction yield and selectivity

| Ex. no. | TMSOTf (eq.) | EtNCO (eq.) | Solvent (procedure)[a] | T, °C. (time, h) | Yield of 1a, % | 1a/9/10[d] |
|---|---|---|---|---|---|---|
| 15 | 1.1 | 3–5 | Toluene (A) | 0(5), rt(24) | 50[c] | 97.7:1.3:1.0 |

[a]Procedures A or B described in example 1;
[b]Crystallized from diethyl ether;
[c]Purified by short silica gel column;
[d]Monitored by HPLC of the crude product.

EXAMPLES 16–23

Scheme 6

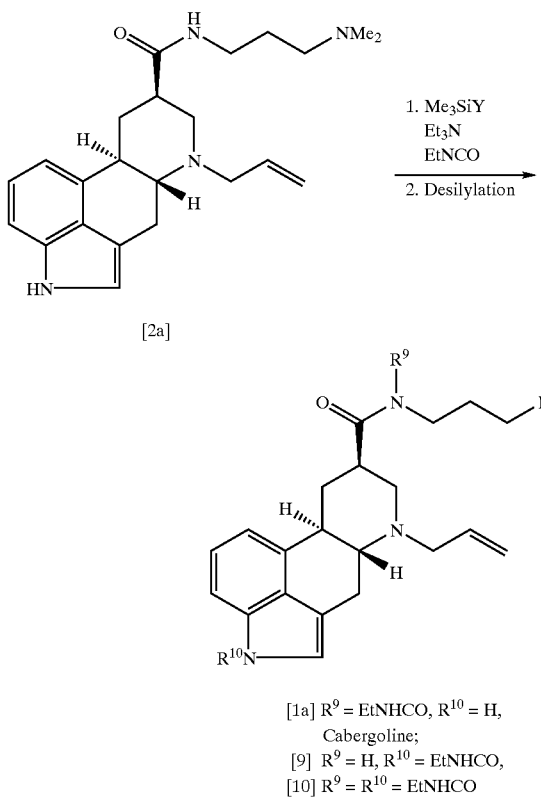

[1a] R[9] = EtNHCO, R[10] = H, Cabergoline;
[9] R[9] = H, R[10] = EtNHCO,
[10] R[9] = R[10] = EtNHCO

TABLE 2

Reaction between [2a] and ethyl isocyanate with different silylating agents according to method A of Example 1.

| Ex. No. | Silylating agent[d] (eq.) | Solvent | T °C., (time, h) | Yield of 1a, % | 1a/9/10[c] |
|---|---|---|---|---|---|
| 16 | HMDS (>2) | CH$_2$Cl$_2$ | 0 (5), reflux (24) | no reaction | |
| 17 | HMDS (>2) | Toluene | 0 (5), reflux (24) | no reaction | |
| 18 | TMSCl (>2) | CH$_2$Cl$_2$ | 0 (5), reflux (24) | 17[b] | 99.0/0/1.0 |
| 19 | TMSCl (>2) | Toluene | 0 (5), reflux (24) | 24[b] | 99.0/0/1.0 |
| 20 | TMSI (1.05) | CH$_2$Cl$_2$ | 0 (5), 10 (24) | 92[a] | 99.6/0/0.4 |
| 21 | TMSBr (1.2) | THF | 50 (24) | 94[a] | 99.4/0.3/0.3 |
| 22 | TMSOBs (1.2) | THF | 50 (24) | 83[b] | 98.7/0.4/0.9 |
| 23 | MTDA (2.0) | MeCN | reflux (24) | 89[a] | 99.7/0/0.3 |

[a]Crystallize from diethyl ether
[b]Purified by short silica gel column
[c]Monitored by HPLC of the crude product
[d]Silylation agents: HMDS—1,1,1,3,3,3-hexamethyldisilazane, TMSCl—trimethylsilyl chloride, TMSI—trimethylsilyl iodide, TMSBr—trimethylsilyl bromide, TMSOBs—trimethylsilyl benzenesulfonate, MTDA—methyl trimethylsilyl dimethylketene acetal.

EXAMPLE 24

Scheme 7

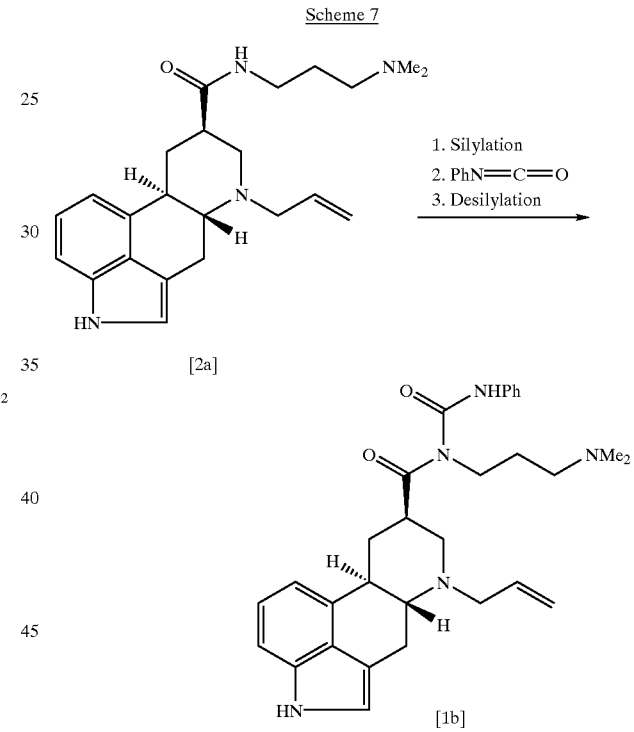

According to the method A of Example 1 compound [1b] was obtained using phenyl isocyanate instead of ethyl isocyanate.

$^1$H NMR (CDCl$_3$, δ, ppm) 9.81 (bs, 1H), 8.22 (s, 1H), 7.73 (d, 2H, J=8.0 Hz), 7.31 (t, 2H, J=8.0 Hz), 7.23–7.01 (m, 3H), 6.87 (m, 2H), 5,92 (m, 1H), 5.23 (d, 1H, J=17.0 Hz), 5.21 (d, 1H, J=9.2 Hz)3.84 (m, 2H), 3.54 (dd, 1H, J=13.0, 4.6 Hz), 3.32 (m, 2H), 3.15 (d, 1H, J=11.3 Hz), 3.00 (t, 1H, J=5.2 Hz), 2.72 (m, 2H), 2.61 (m, 2H), 2.49 (t, 2H, J=6.6 Hz), 2.14 (s, 3H), 1.83–1.74 (m,3H).

What is claimed is:

1. A process for the preparation of a compound of the formula [I]:

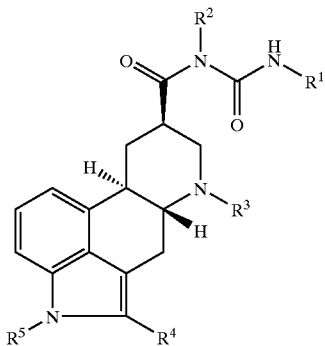

stereoisomers of the compound of formula [I] or acid addition salts thereof, wherein $R^1$ is selected from the group consisting of alkyl having from 1 to 4 carbon atoms, cyclohexyl, phenyl, and dimethylamino alkyl group —$(CH_2)_nNMe_2$ in which n is an integer from 2 to 6, $R^2$ is selected from the group consisting of hydrogen, alkyl having from 1 to 4 carbon atoms, cyclohexyl, phenyl, dimethylamino alkyl group —$(CH_2)_nNMe_2$ in which n is an integer from 2 to 6, pyridyl, pyrimidyl, pyrazinyl, pyridazinyl, thiazolyl and thiadiazolyl, $R^3$ represents a hydrocarbon group having from 1 to 4 carbon atoms, and $R^4$ is selected from the group consisting of hydrogen, halogen, methylthio and phenylthio group; which process comprises silylating with a silylation agent a compound represented by the formula [2]:

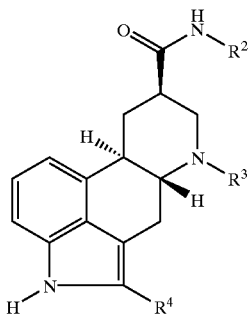

stereoisomers of the compound represented by formula [2] or metal or ammonium salts or acid addition salts thereof, wherein $R^2$, $R^3$ and $R^4$ are as defined above, and reacting the resultant product with a compound represented by the formula [5]:

$R^1$—N=C=O     [5]

wherein $R^1$ is as defined above, followed by desilylation.

2. A process according to claim 1, wherein said silylation is carried out by contacting a compound [2], stereoisomers as well as metal or ammonium salts or acid addition salts thereof with a silylating agent represented by the formula [3]:

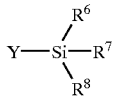

wherein $R^6$, $R^7$ and $R^8$ may be the same or different and are selected from the group consisting of alkyl having from 1 to 6 carbon atoms, aryl and aralkyl radicals; Y is selected from the group consisting of chloro, bromo, iodo, (haloalkyl)sulfonyloxy, alkylsulfonyloxy, arylsulfonyloxy, (trialkylsilyloxy)-sulfonyloxy, imidazolyl, N-acyl-N-alkylamino, N-acyl-N-(trialkylsilyl) amino, (trialkylsilyl)amino, N,N-dialkylamino, isopropenyloxy, 1-alkoxy-1-propenyloxy and trichloroacetoxy radicals; to give intermediate compound represented by the formula [4]:

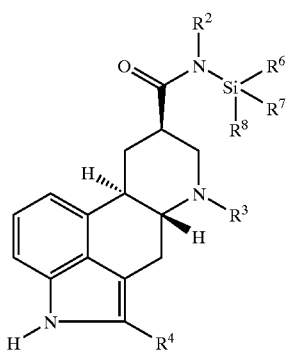

tautomers or mixtures thereof, stereoisomers, as well as acid addition salts thereof wherein $R^2$, $R^3$, $R^4$, $R^6$, $R^7$ and $R^8$ are as defined above, which react with compound [5] to give a compound represented by the formula [6]:

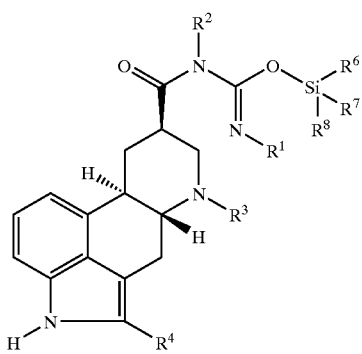

tautomers or mixtures thereof, stereoisomers, as well as acid addition salts thereof, wherein $R^1$, $R^2$, $R^3$, $R^4$, $R^6$, $R^7$ and $R^8$ are as defined above; following desilylation thereof to obtain the desired compound [I] or acid addition salts thereof.

3. A process according to claim 1, wherein $R^1$ is ethyl, $R^2$ is dimethylaminopropyl, $R^3$ is allyl group, $R^4$ is hydrogen, and $R^6$, $R^7$ and $R^8$ are methyl groups.

4. A process according to claim 1, which is carried out in an aprotic organic solvent.

5. A process according to claim 4, wherein the solvent is an aromatic hydrocarbon, a hydrocarbon halide, an ether solvent, an ester solvent or a highly polar aprotic organic solvent.

6. A process according to claim 5, wherein the solvent is dichloromethane, chloroform, toluene, ether, isopropyl ether, tert-butyl methyl ether, 1,2-dimethoxyethane, 1,2-diethoxyethane, tetrahydrofurane (THF), ethyl acetate, isopropyl acetate, butyl acetate, acetonitrile, N,N-dimethylformamide (DMF), N,N-dimethylacetamide or 1-methylpyrrolidinone (NMP).

7. A process according to claim 1, wherein the silylating agent is selected from the group consisting of trimethylsilyl trifluoromethanesulfonate, trimethylsilyl methanesulfonate, trimethylsilyl benzenesulfonate, trimethylsilyl chlorosulfonate, trimethylsilyl chloride, bromide, iodide, trichloroacetate or trifluoroacetate, 1-(trimethylsilyl)imidazol, 1-(trimethylsilyl)-1,2,4-triazole, 1-(trimethylsilyl)-1H -benzotriazole, 1-(trimethylsilyl)2-pyrrolidinone, N-methyl-N-(trimethylsilyl)sulfate, N,O-bis(trimethylsilyl)acetamide and bis(trimethylsilyl)trifluoroacetamide.

8. A process according to claim 1, wherein 1 to 5-fold molar amount of silylating agent relative to compound [2] is used for silylating of compound [2].

9. A process according to claim 2, wherein 1 to 5-fold molar amount of silyating agent [3] relative to compound [2] is used for silylating of compound [2].

10. A process according to claim 1, wherein said silylation is carried out in the presence of organic bases or salts.

11. A process according to claim 2, wherein said silylation is carried out in the presence of organic bases or salts.

12. A process according to claim 10, wherein said organic bases are tertiary amines, sterically hindered secondary amines, pyridine or their derivatives, 1, 5-diazabicyclo[4.3.0]non-5-ene(DBN),1,8-diazabicyclo[5.4.0]undec-7-ene (DBU) or mixtures thereof.

13. A process according to claim 12, wherein said tertiary amines are selected from the group consisting of 1-ethylpiperidine, 1-butylpyrrolidine, diisopropylethylamine, triethylamine, N,N,N',N'-tetramethylethylenediamine, 1,4-diazabicyclo[2.2.2]octane and mixtures thereof.

14. A process according to claim 12, wherein said sterically hindered secondary amines are selected from the group consisting of diisopropylamine, dicyclohexylamine, 2,2,6,6-tetramenthylpiperidine and mixtures thereof.

15. A process according to claim 12, wherein said pyridine derivatives are 4-dimethylaminopyridine (DMAP), 4-(4-methylpiperidino)pyridine and 4-pyrrolidinopyridine or a mixture thereof.

16. A process according to claim 10, wherein said salts are selected from the group consisting of metal halides, tertiary ammonium halides, ammonium halides, ammonium sulfate and pyridine or its derivatives hydrohalides and mixtures thereof.

17. A process according to claim 10, wherein said acids are selected from the group consisting of p-toluenesulfonic acid, methanesulfonic acid, sulfuric acid and hydrogen halides.

18. A process according to claim 1, wherein the compound [5] is used in a 1-to 5-fold molar amount relative to the compound [2].

19. A process according to claim 2, wherein the compound [5] is used in a 1-to 5-fold molar amount relative to the compound [2].

20. A process according to claim 1 wherein n is 3.

* * * * *